(12) United States Patent
Yi et al.

(10) Patent No.: US 9,101,388 B2
(45) Date of Patent: Aug. 11, 2015

(54) SAFETY SCALPEL WITH REPLACEABLE BLADE CARTRIDGE AND SAFETY BRAKE

(75) Inventors: Patrick Yi, Roswell, GA (US); Hong-Minh Le, Singapore (SG)

(73) Assignee: MEDIPURPOSE PTE LTD. (SG)

( * ) Notice: Subject to any disclaimer, the term of this patent is extended or adjusted under 35 U.S.C. 154(b) by 627 days.

(21) Appl. No.: 12/520,225

(22) PCT Filed: Dec. 19, 2007

(86) PCT No.: PCT/US2007/088054
§ 371 (c)(1),
(2), (4) Date: Jul. 31, 2009

(87) PCT Pub. No.: WO2008/077084
PCT Pub. Date: Jun. 26, 2008

(65) Prior Publication Data
US 2010/0036404 A1   Feb. 11, 2010

Related U.S. Application Data

(63) Continuation-in-part of application No. 11/613,065, filed on Dec. 19, 2006, now Pat. No. 8,015,712.

(51) Int. Cl.
*A61B 17/32*       (2006.01)
*A61B 17/3213*    (2006.01)
(Continued)

(52) U.S. Cl.
CPC ... *A61B 17/3213* (2013.01); *A61B 2017/32113* (2013.01); *A61B 2019/4805* (2013.01); *Y10T 29/49826* (2013.01)

(58) Field of Classification Search
USPC ........ 30/162, 163, 335, 336, 2, 339; 606/167, 606/170
IPC .............................. A61B 17/3213; B26B 29/02
See application file for complete search history.

(56) References Cited

U.S. PATENT DOCUMENTS 5,269,063 A   12/1993 Okada
5,299,357 A    4/1994 Wonderley et al.
(Continued)

FOREIGN PATENT DOCUMENTS

EP    0958788    11/1999
EP    1031322     8/2000
(Continued)

OTHER PUBLICATIONS

EPO Office Action dated Jul. 9, 2010 for related European Application No. 05818143.9.
(Continued)

*Primary Examiner* — Kenneth E. Peterson
(74) *Attorney, Agent, or Firm* — Troutman Sanders LLP; Ryan A. Schneider; Benjamin C. Wiles

(57) ABSTRACT

A safety scalpel that incorporates a reusable metal scalpel handle (500) similar in shape and feel to the conventional metal handle preferred by most surgeons, and a disposable blade cartridge (300) that covers the blade (100) before, during and after use, and is easily mounted and released from the scalpel handle. The blade cartridge includes a blade (100) with similar cutting profiles as standard surgical blades, a blade holder that is permanently fixed to the blade, and a blade guard (300) that covers the blade and within which the blade holder (200) is able to slide. The scalpel handle is reusable, while the blade cartridge is disposable. The blade cartridge is attachable and detachable from the scalpel handle and may include a mechanical brake (1301) to prevent movement of the blade except when the reusable handle is in place. A safety latch feature (2230) is provided.

13 Claims, 16 Drawing Sheets

(51) Int. Cl.
*A61B 17/3211* (2006.01)
*A61B 19/00* (2006.01)

(56) References Cited

U.S. PATENT DOCUMENTS

| | | | |
|---|---|---|---|
| 5,330,493 | A | 7/1994 | Haining |
| 5,342,379 | A | 8/1994 | Volinsky |
| 5,741,289 | A | 4/1998 | Jolly et al. |
| 5,868,771 | A | 2/1999 | Herbert et al. |
| 5,924,206 | A | 7/1999 | Cote et al. |
| 5,938,676 | A * | 8/1999 | Cohn et al. ............. 606/167 |
| 5,941,892 | A | 8/1999 | Cohn et al. |
| 6,022,364 | A | 2/2000 | Flumene et al. |
| 6,053,929 | A | 4/2000 | Cohn et al. |
| 6,254,621 | B1 | 7/2001 | Shackelford et al. |
| 6,589,258 | B2 | 7/2003 | Pilo et al. |
| 6,629,985 | B1 * | 10/2003 | Kiehne ............. 606/167 |
| 6,757,977 | B2 | 7/2004 | Dambal et al. |
| 6,884,240 | B1 | 4/2005 | Dykes |
| 7,153,317 | B2 * | 12/2006 | Kanodia et al. ......... 606/167 |
| 7,172,611 | B2 | 2/2007 | Harding et al. |
| 7,207,999 | B2 | 4/2007 | Griffin et al. |
| 7,346,989 | B2 * | 3/2008 | Shi ............. 30/151 |
| 7,669,337 | B2 | 3/2010 | Yi et al. |
| 7,857,824 | B2 * | 12/2010 | Kiehne ............. 606/167 |
| 8,015,712 | B2 * | 9/2011 | Yi et al. ............. 30/162 |
| 8,114,103 | B2 * | 2/2012 | Rasco ............. 606/167 |
| 2006/0095057 | A1 | 5/2006 | Yi et al. |
| 2006/0212058 | A1 * | 9/2006 | Djordjevic et al. ........ 606/167 |
| 2009/0131963 | A1 * | 5/2009 | Rasco ............. 606/172 |
| 2010/0036404 | A1 * | 2/2010 | Yi et al. ............. 606/167 |
| 2010/0063522 | A1 * | 3/2010 | Reaux ............. 606/167 |

FOREIGN PATENT DOCUMENTS

| | | |
|---|---|---|
| JP | 6021745 | 2/1985 |
| JP | 63172411 | 11/1998 |
| JP | 11318914 | 11/1999 |
| JP | 2003339723 | 12/2003 |
| WO | 2006049991 | 5/2006 |
| WO | WO 2008/077084 | 6/2008 |

OTHER PUBLICATIONS

Office Action of the Intellectual Property Office of Taiwan dated Sep. 13, 2011 for related Taiwan Patent Application No. 094137706.
The Notification of the First Office Action dated Jun. 7, 2010 issued by the State Intellectual Property Office of P.R. China for related Chinese Application No. 200780045244.X.
International Search Report dated Mar. 3, 2006 for Related Application No. PCT/US2005/038588.
International Search Report and Written Opinion dated May 13, 2008 for Related Application No. PCT/US2007/088054.
Preliminary Notice of Rejection dated Dec. 21, 2010 for related Japanese Application No. 2007-539071.
Office Action issued by JPO dated Jun. 26, 2012 for related Japanese Patent Application No. 2009-543167.

* cited by examiner

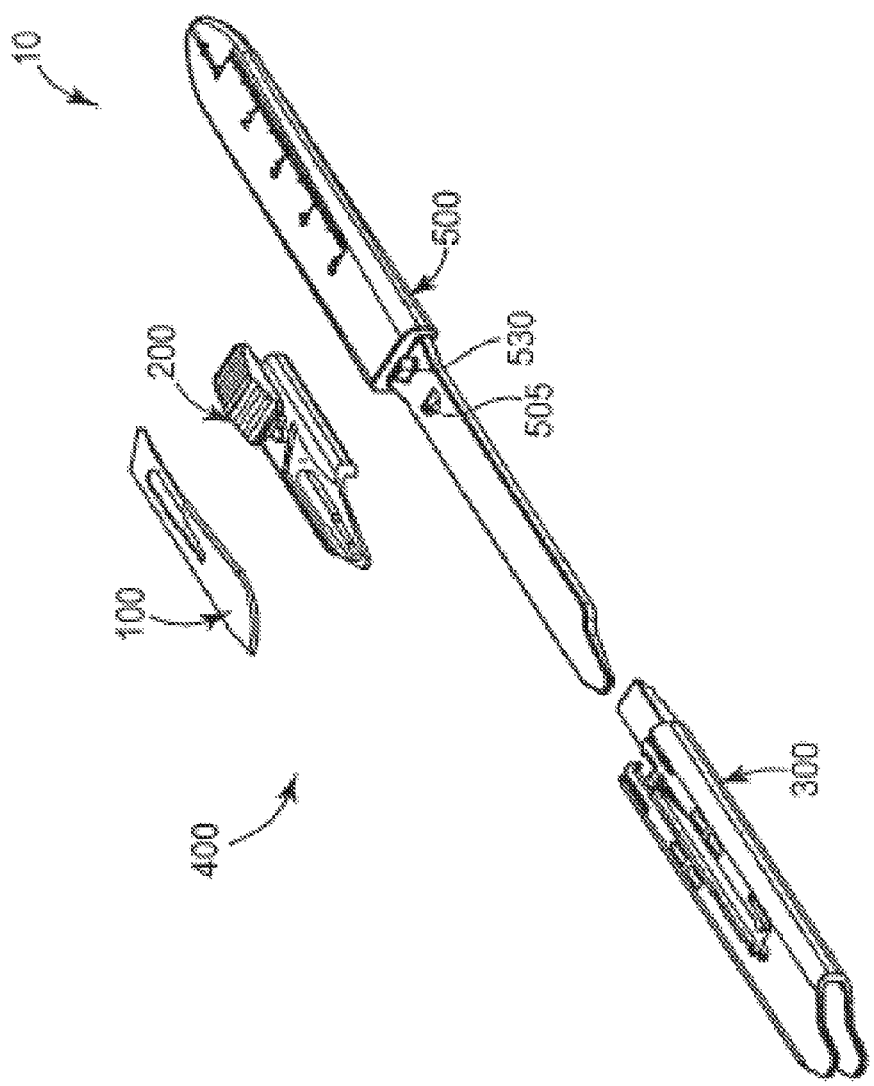

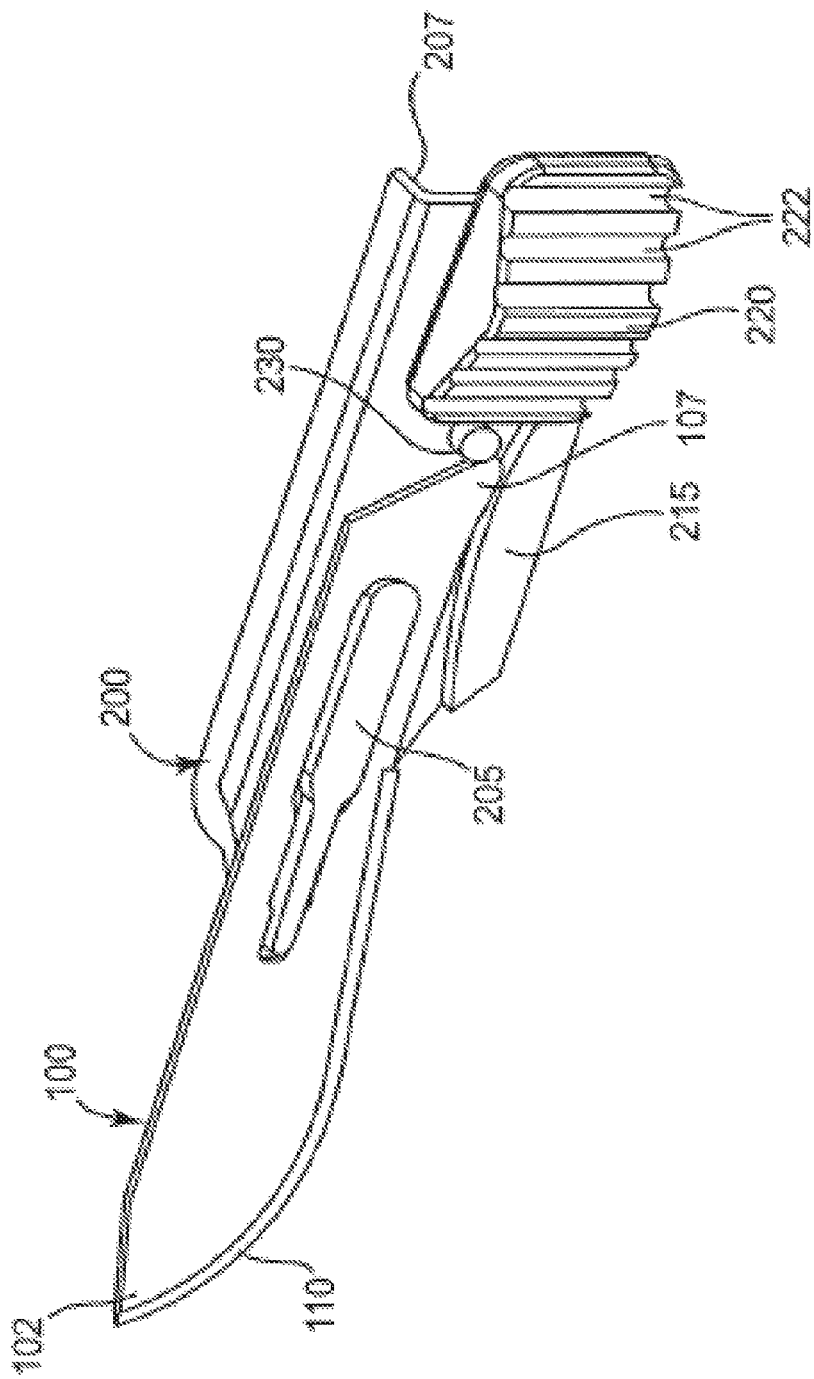

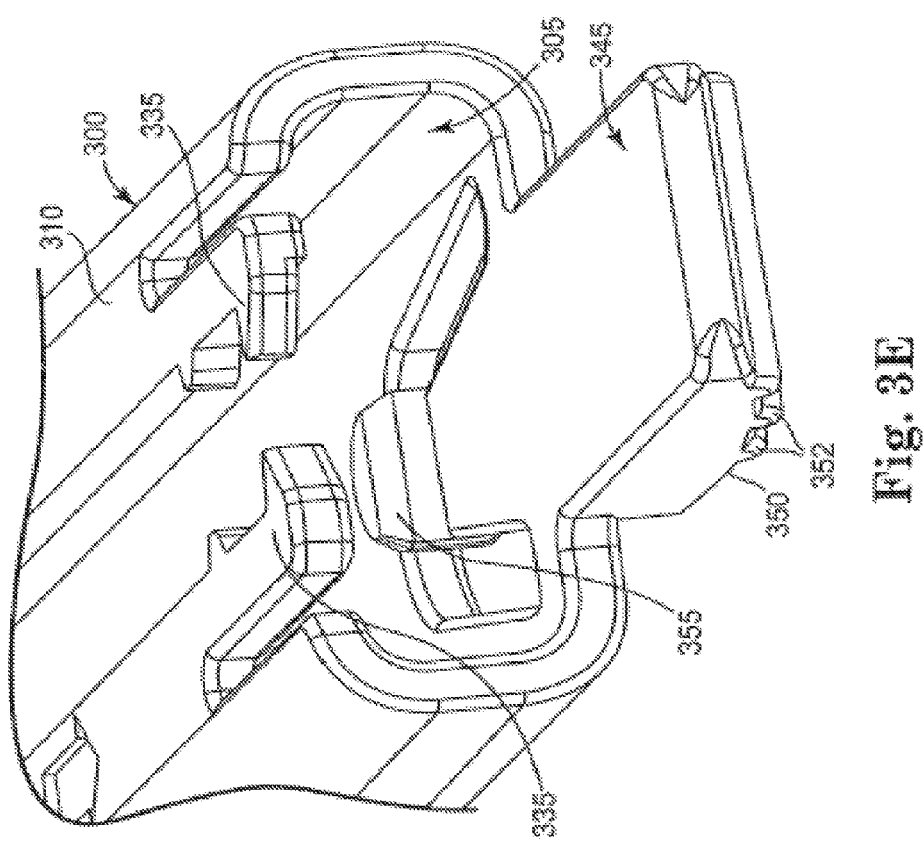

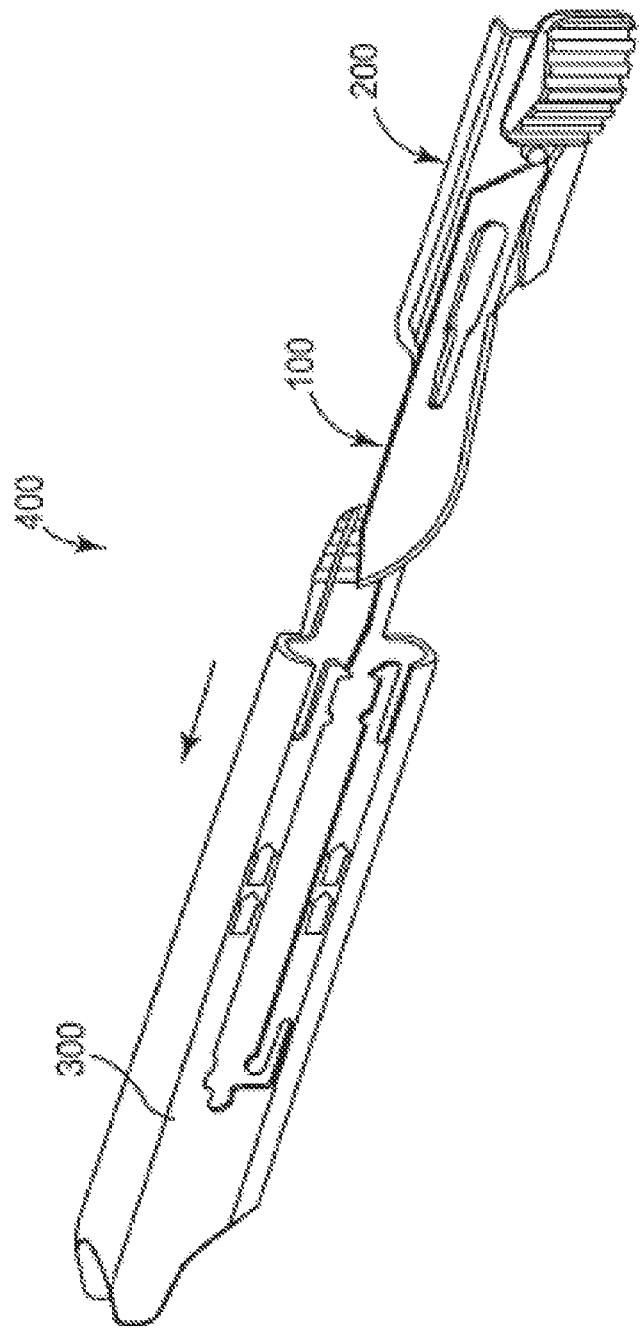

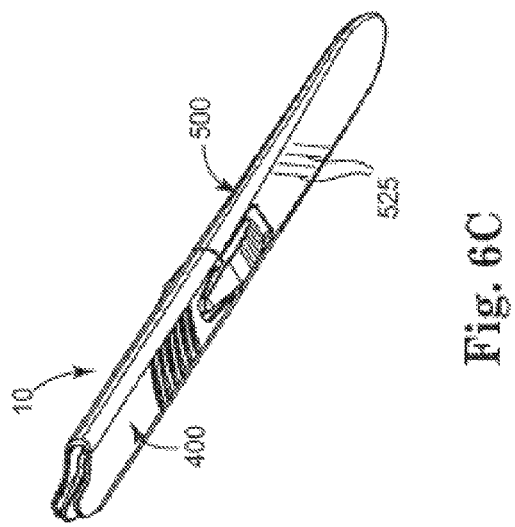
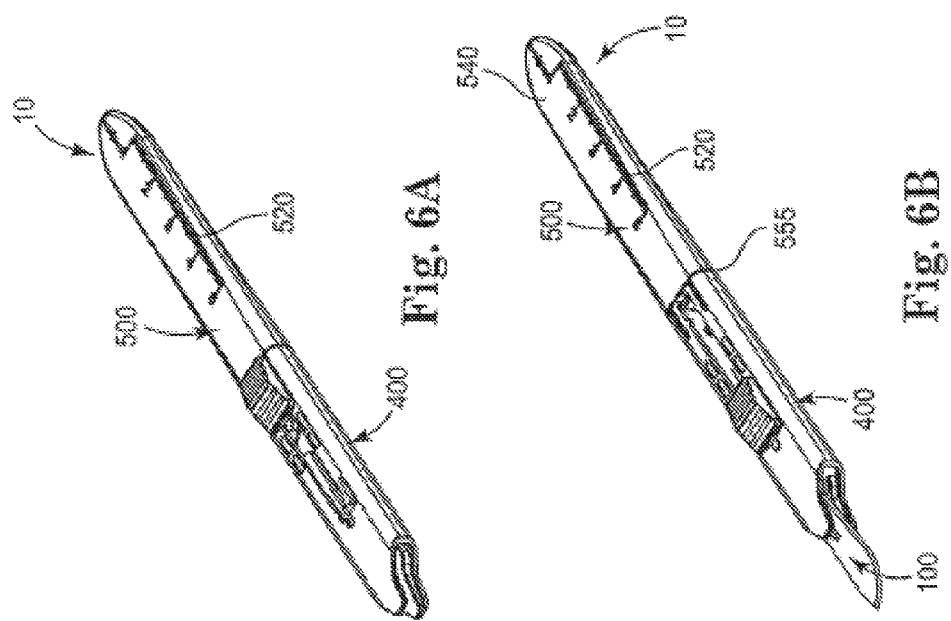

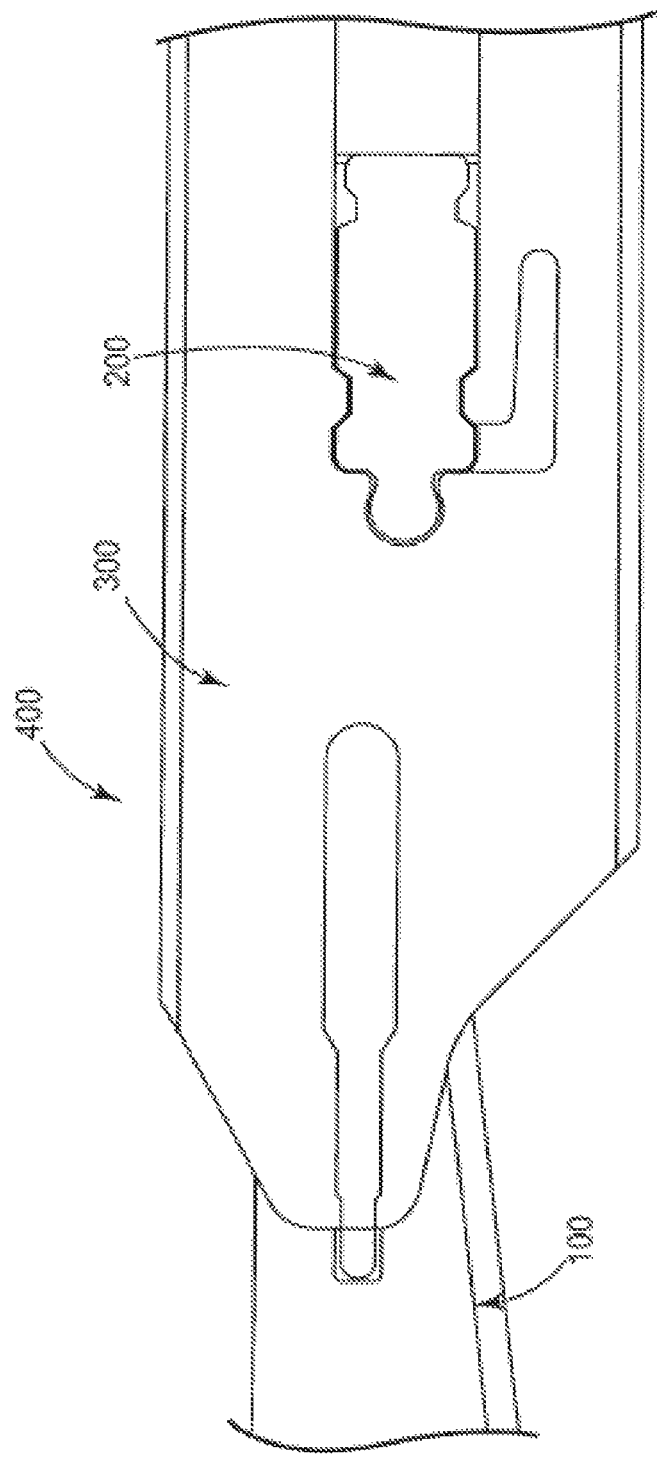

SAFETY SCALPEL WITH REPLACEABLE BLADE CARTRIDGE AND SAFETY BRAKE

CROSS REFERENCE TO RELATED APPLICATION AND CLAIM OF BENEFIT

This application is a US National Stage of International Patent Application No. PCT/US2007/088054, filed 19 Dec. 2007, which is a continuation-in-part of U.S. patent application Ser. No. 11/613,065, filed 19 Dec. 2006, now U.S. Pat. No. 8,015,712.

FIELD OF THE INVENTION

The present invention relates generally to scalpel devices and, in particular, to safety scalpels for medical use.

BACKGROUND OF THE INVENTION

Health care is the second fastest growing sector of the U.S. economy, employing over 12 million workers. Health care workers face a wide range of hazards on the job, including needlestick and sharps injuries, back injuries, latex allergies, violence, and stress. Although it is possible to prevent or reduce health care worker exposure to these hazards, health care workers are actually experiencing increasing numbers of occupational injuries and illnesses. Rates of occupational injury to health care workers have risen over the past decade. By contrast, two of the most hazardous industries, agriculture and construction, are safer today than they were a decade ago.

Precise national data is not available on the annual number of needlestick and other percutaneous injuries among health care workers; however, estimates indicate that 600,000 to 800,000 such injuries occur annually. About half of these injuries go unreported. Data from EPINet (the Exposure Prevention Information Network) suggests that at an average hospital, workers incur approximately thirty needlestick injuries per 100 beds per year.

Most reported needlestick and sharps injuries involve nursing staff; but laboratory staff, physicians, housekeepers, and other health care workers are also injured. Some of these injuries expose workers to bloodborne pathogens that can cause infection. The more serious of these pathogens are the hepatitis B virus (HBV), the hepatitis C virus (HCV), and the human immunodeficiency virus (HIV). Infections by each of these pathogens are potentially life threatening, yet preventable.

The emotional impact of needlestick and sharps injuries can be severe and long lasting, even when a serious infection is not transmitted. This impact is particularly severe when the injury involves exposure to HIV. In one study of twenty health care workers with an HIV exposure, eleven reported acute severe distress, seven had persistent moderate distress, and six quit their jobs as a result of the exposure. Other stress reactions requiring counseling have also been reported. Not knowing the infection status of the source patient can accentuate the health care worker's stress. In addition to the exposed health care worker, colleagues and family members may suffer emotionally.

Safety and health issues can best be addressed in the setting of a comprehensive prevention program that considers all aspects of the work environment and that has employee involvement as well as management commitment. Implementing the use of improved engineering controls is one component of such a comprehensive program. Other prevention strategy factors that must be addressed, however, include modification of hazardous work practices, administrative changes to address needle hazards in the environment (e.g., prompt removal of filled sharps disposal boxes), safety education and awareness, feedback on safety improvements, and action taken on continuing problems.

Improved engineering controls are often among the most effective approaches to reducing occupational hazards and, therefore, are an important element of a needlestick prevention program. Such controls include eliminating the unnecessary use of needles and implementing devices having safety features. A number of sources have identified several desirable characteristics for safety devices, which include preferences for safety devices that: do not use needles; incorporate the safety feature as an integral part of the device; work passively (i.e., requires no activation by the user); have a safety feature that can be engaged with a single-hand technique and allows the worker's hands to remain behind the exposed sharp, if user activation is necessary; allow the user to easily determine whether the safety feature is activated; have a safety feature that cannot be deactivated and remains protective through disposal; perform reliably; are easy to use and practical; and are safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merit and ultimately on its ability to reduce workplace injuries.

Regarding specifically scalpels, the conventional scalpel currently used in the healthcare industry includes a metal handle and a disposable blade that is mounted on the handle prior to use, and removed after use. The process of mounting and dismounting of the blade is a difficult and dangerous procedure, which exposes the medical practitioner to potential injury from the exposed blade and contamination due to blood that may be present on the blade. Further, sharps injuries may also occur during an operation as the surgeon passes the exposed scalpel to a colleague.

Surgeons who have developed a feel for the shape and weight of the metal handle dislike the current disposable safety scalpels as, among other things, the plastic handle is too light and feels "different." During use, the plastic handle of the scalpel incurs undesirable flexibility than that of a metal handle scalpel. In addition, the disposable safety scalpel is significantly more expensive than the regular disposable blade. These two factors currently limit the adoption of safety scalpels in the healthcare industry.

What is needed is a safe and reliable scalpel that overcomes the present objections from the healthcare practitioner of current designs, while providing adequate protection for the medical workers handling the scalpel. It is to such a device that the present invention is primarily directed.

SUMMARY OF THE INVENTION

Briefly described, in a preferred form, the present invention is an improvement over the conventional scalpel by providing a safety scalpel that incorporates a reusable metal scalpel handle similar in shape and feel to the conventional metal handle preferred by most surgeons, and a disposable blade cartridge that covers the blade before, during, and after use, and is easily mounted and released from the metal scalpel handle.

The present safety scalpel comprises a blade with similar cutting profiles as standard surgical blades, a blade holder that is fixed to the blade, a blade guard that covers the blade and within which the blade holder is able to slide, a scalpel handle that receives a blade cartridge (being the blade, blade holder and blade guard assembled together), and a locking assembly. The scalpel handle is reusable, while the blade cartridge is disposable.

While prior art designs have incorporated disposable blade cartridges where the blade guard slides off the releaseably fixed blade, the present invention is based on the blade sliding out of the releaseably fixed guard.

The present invention comprises a safety disposable blade cartridge that can be used with either a preferably reusable metal, or disposable plastic, scalpel handle, having the weight and feel of conventional designs. The blade cartridge easily fixes onto the scalpel handle, and yet is securely and releasably locked on the scalpel handle. The blade is preferably movable through at least three distinct positions—open, closed, and locked.

Attaching and detaching the blade cartridge to the scalpel handle utilizes an easy, longitudinal sliding motion. When fixed to the scalpel handle, only the blade and blade holder of the blade cartridge can move in a longitudinal direction, as the blade guard experiences limited or no longitudinal movement.

In other preferred embodiments, the blade cartridge is itself a standalone mini-scalpel, which is securely fixed to a passive metal handle or the blade can move within a hollow metal holder.

In still other embodiments, the blade is immobilized against movement when the reusable handle is removed.

A method of operation and construction is also provided herein.

For example, there is disclosed a safety scalpel having, a disposable blade cartridge which has a blade, a blade holder in communication with the blade; and a blade guard adapted to receive the blade and blade holder; and a non-disposable scalpel handle having a distal end, wherein the disposable blade cartridge is slideable onto the distal end of the non-disposable scalpel handle, the disposable blade cartridge for lockable to the non-disposable scalpel handle.

The safety scalpel may also include a catch for engaging the extending member, and wherein the catch engaging the extending member locks the disposable blade cartridge to the scalpel handle.

The scalpel of may also have a blade holder with a holder knob, the blade moveable from a closed position, wherein the blade is not exposed beyond the disposable blade cartridge, to an open position, and wherein the blade is exposed beyond the disposable blade cartridge.

The safety scalpel may also include an extending member, wherein the disposable blade cartridge includes a catch for engaging the extending member, wherein the catch engaging the extending member locks the disposable blade cartridge to the scalpel handle, and wherein the blade holder further comprises a holder knob, the holder knob enabling the blade to move from a closed position, wherein the blade is not exposed beyond the disposable blade cartridge, to an open position, wherein the blade is exposed beyond the disposable blade cartridge.

The scalpel may also include a latching assembly comprising a locking mechanism that is adapted to engage an aperture of the scalpel handle, such that the latching assembly locks the blade cartridge to the scalpel handle.

Another embodiment of the scalpel may also include a mechanical brake to supply frictional force to prevent movement of the blade and the brake make at least one element which supplies frictional force to prevent movement of the blade only when the handle is removed.

The scalpel may includes a space for receiving said handle and wherein said brake element includes a finger which flexibly protrudes into said space allowed for the handle, whereby the brake is prevented from interfering with the movement of the blade and the finger may be configured to flexibly engage at least a portion of the blade holder when said handle is not in place, thereby preventing movement of the blade without the handle.

The scalpel may include a finger with a contact land, said land having a chamfered surface proximate the point where said land contacts said blade holder when so engaged.

The scalpel may further include a locking safety feature of a safety catch for preventing accidental retraction of the blade when in use, having a slider knob at least partly external to the blade guard and in mechanical communication with the blade, so that movement of the slider causes movement of the blade, said slider including a base portion and releaseable engagement portion, a catch portion sized to receive said engagement portion, said catch located on said guard such that said catch and engagement portion are engaged when the blade is in a fully extended position.

In addition the safety feature may include a resilient portion extending from said base, having a free end and being spaced apart from said base. The resilient portion may arcuate and depressible and include a catch at its free end and wherein said catch portion includes a receiver sized to receive said catch, so that when said resilient portion is undepressed, said catch may be engaged within said receiver thereby preventing movement of the blade.

The scope of the invention is determined by the claims and this summary is only intended to give the reader a preview of the remainder of the entire specification.

BRIEF DESCRIPTION OF THE DRAWINGS

FIG. 1B illustrates a perspective view of a safety scalpel in accordance with another preferred embodiment of the present invention;

FIG. 2B illustrates a perspective view of the assembled blade and blade holder of FIG. 2A;

FIG. 3E illustrates a perspective view from a proximal end of the blade guard of FIG. 3C;

FIG. 4 illustrates a perspective view of assembly of a blade cartridge in accordance with a preferred embodiment of the present invention;

FIG. 6A illustrates a perspective view of a front face of a safety scalpel with the blade housed in the blade cartridge, in accordance with a preferred embodiment of the present invention;

FIG. 6B illustrates a perspective view of the front face of the safety scalpel of FIG. 6A with the blade extending from the blade cartridge, in accordance with a preferred embodiment of the present invention;

FIG. 6C illustrates a perspective view of a back face of the safety scalpel of FIG. 6A with the blade housed in the blade cartridge, in accordance with a preferred embodiment of the present invention;

FIG. 7 illustrates a close-up, front face view of a distal end of a blade cartridge with a blade extending from a blade guard, in accordance with a preferred embodiment of the present invention;

DETAILED DESCRIPTION

Figure 1A:
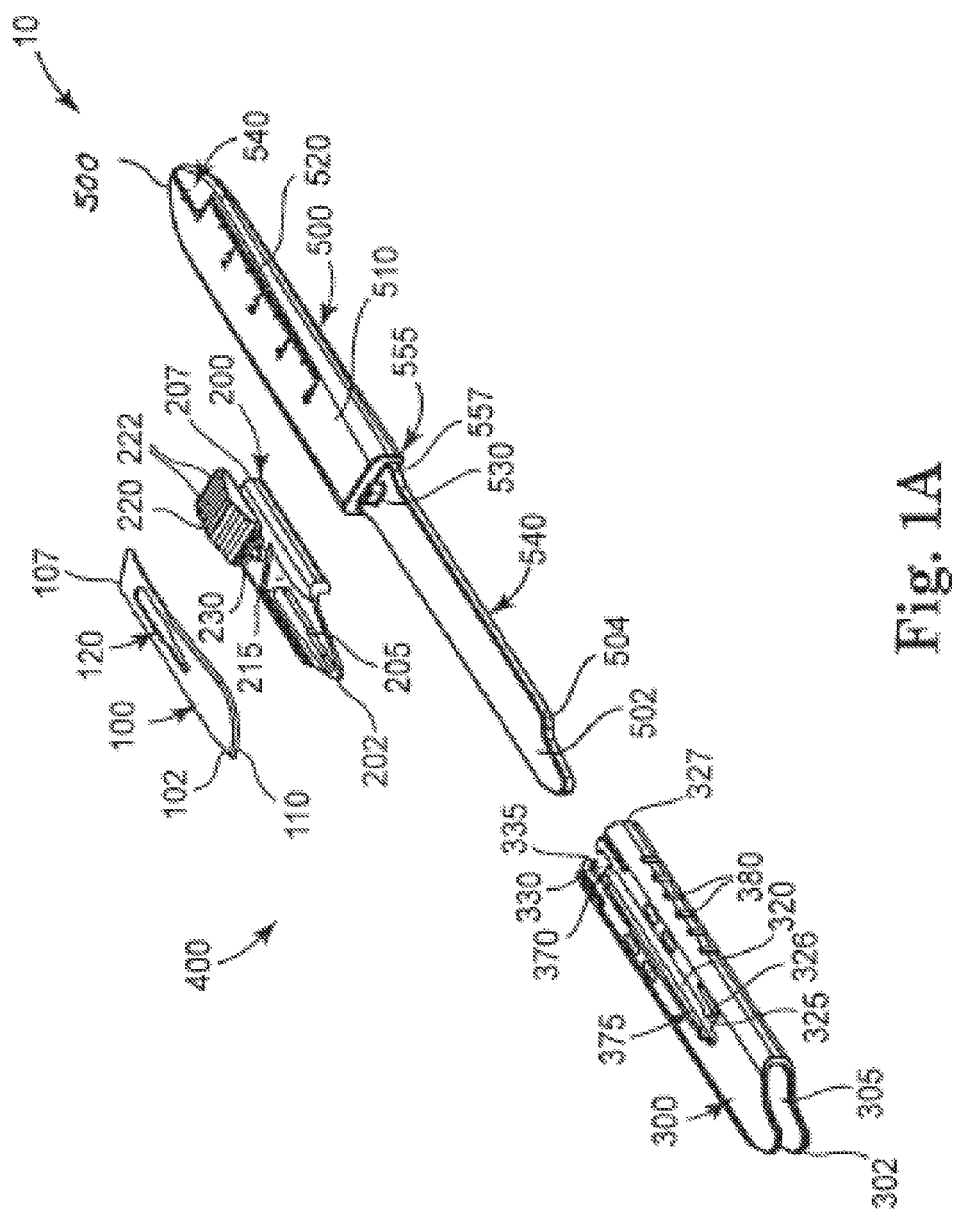
FIG. 1A illustrates a perspective view of a safety scalpel in accordance with a preferred embodiment of the present invention.

Referring now in detail to the figures, wherein like reference numerals represent like parts throughout the several views, the present safety scalpel 10 of FIGS. 1A, 1B, and 6A-6C, comprises a blade 100 is fixable to a blade holder 200, which subassembly is slideable within a blade guard 300. The combination of the blade 100, the blade holder 200, and the blade guard 300 forms a blade cartridge 400, attachable to a scalpel handle 500.

The present safety scalpel 10 comprises the blade cartridge 400 and the scalpel handle 500, such that the blade cartridge 400 is configured for secure attachment to and safe detachment from the scalpel handle 500. In a preferred embodiment of the present invention, the blade cartridge 400 is disposable, while the scalpel handle 500 is non-disposable. Accordingly, a new blade cartridge 400 can be attached to the scalpel handle 500 for use by, for example, a medical practitioner. After the medical practitioner has finished using the safety scalpel 10, the blade cartridge 400 can be safely removed from the scalpel handle 500, so that the blade cartridge 400 can be disposed of properly.

The blade cartridge 400 can comprise the blade 100, the blade holder 200 adapted to securely engage the blade 100, and the blade guard 300 configured to slideably receive the blade 100 and blade holder 200. Further, the blade holder 200 is adapted to move the blade 100, or a portion thereof, between a closed and open position. In the closed position, the blade 100 is safely and fully contained within the blade guard 300. In the open position, the blade 100, or a portion thereof, extends beyond the blade guard 300. As designed, the blade 100 is in the closed position during non-use of the safety scalpel 10 and in the open position during active use of the safety scalpel 10. The safety scalpel 10 of the present invention, therefore, provides a safe and effective surgical tool.

Figure 2A:
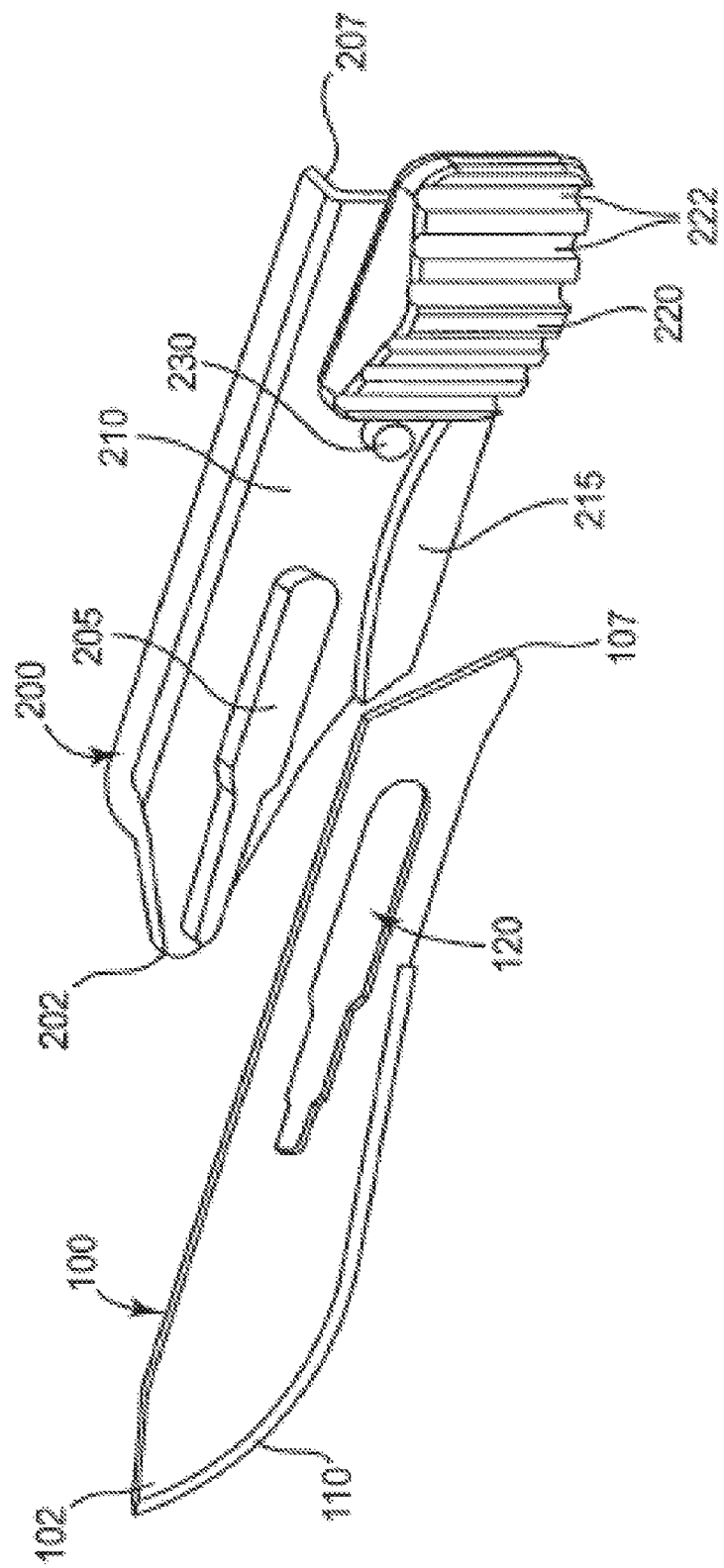
FIG. 2A illustrates a perspective view of an unassembled blade and a blade holder in accordance with a preferred embodiment of the present invention.

As illustrated in FIGS. 2A and 2B, the blade 100 includes a cutting edge 110 located at a distal end 102 of the blade 100. Further, at a proximal end 107, the blade 100 defines an aperture 120; preferably an elongated aperture 120 such as a slot. Other than perhaps the profile of the cutting edge 110, the blade 100 preferably has a similar front and back face.

One skilled in the art will recognize that the blade 100 can be made of a variety of suitable materials including, but not limited to, both carbon and stainless steel. Generally, the carbon and stainless steel used to create the blade 100 are manufactured in compliance with several industry standards including British Standard ("BS") 2982:1992, International Organization for Standardization ("ISO") 7740:1985 and European Standard ("EN") 27740:1992. The blade 100 further can be sterilized by, for example, gamma radiation.

The blade holder 200 is designed to mate with blade 100. Unlike the blade 100, the front face 210 and back/rear face 225 of the blade holder 200 are dissimilar, and the thickness of the blade holder 200 is non-uniform. A distal end 202 of blade holder 200 comprises a holder protrusion 205 extending from the front face 210 of the blade holder 200, in a profile that generally corresponds to the aperture 120 of the blade 100. The holder protrusion 205 is adapted to be securely engaged in the aperture 120 of the blade 100.

The blade holder 200 can further comprise a protrusion notch 215 located on a proximal end of the holder protrusion 205, such that the protrusion notch 215 locks the blade 100 to the blade holder 200. As the holder protrusion 205 engages the blade aperture 120, the blade 100 preferably snaps into the protrusion notch 215, thereby preventing the blade 100 from accidentally disengaging with the blade holder 200.

The blade holder 200 further comprises, at a proximal end 207, a holder knob 220 extending from the front face 210 of the blade holder 200. The surface of holder knob 220 can include a number of ridges 222 for increased traction when in contact with a finger during use of the safety scalpel 10. As described more fully below, the holder knob 220 is adapted to move the blade 100 between the closed and open positions when in communication with the blade guard 300.

Figure 2C:
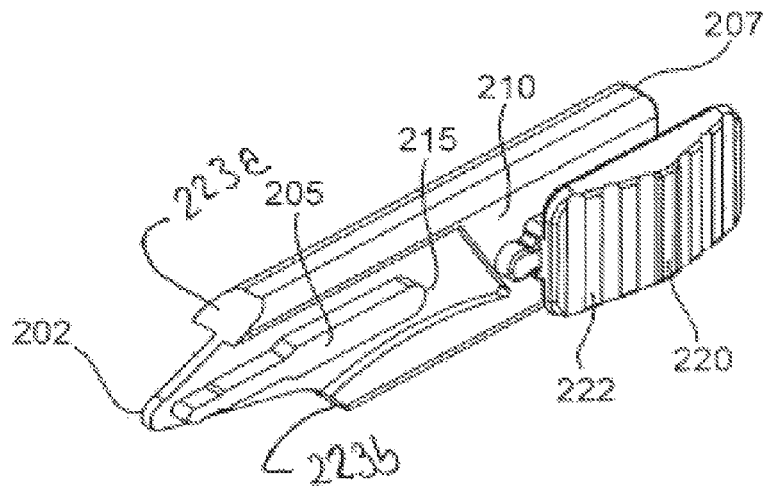
FIG. 2C illustrates a perspective view of a front face of a blade holder in accordance with preferred embodiment of the present invention.
Figure 2D:
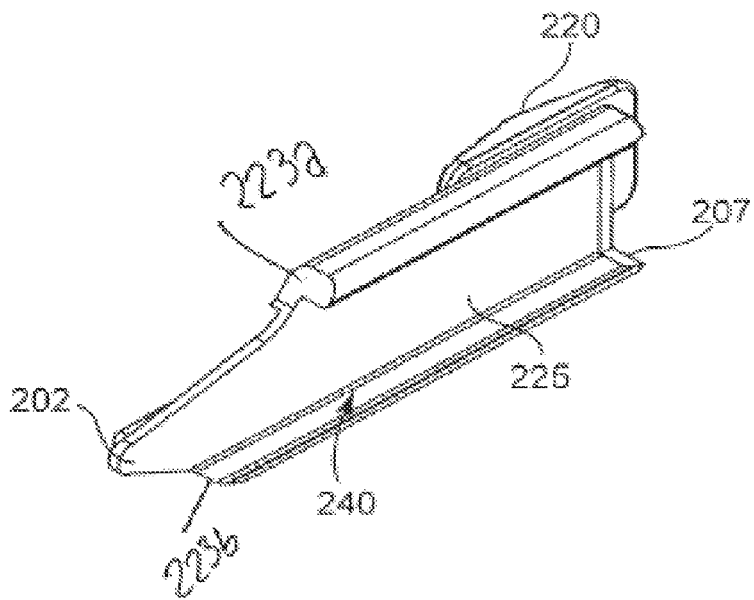
FIG. 2D illustrates a perspective view of a back face of the blade holder of FIG. 2C.

The rear face 225 (see FIG. 2D) of the blade holder 200 can include a track 240 for receiving the scalpel handle 500, preferably the blade receiving portion 550 of the scalpel handle 500. The track 240 defines lateral movement of the blade cartridge 400 when secured to the scalpel handle 500.

As illustrated in FIGS. 3A-3E and 4, the blade guard 300 is designed to slideably receive the blade 100 and blade holder 200. When the blade 100 is in the closed position, the blade guard, or blade sheath, 300 adequately surrounds the blade 100, so that the blade 100 cannot inadvertently cut, puncture, or otherwise damage materials or individuals.

Figure 3A:
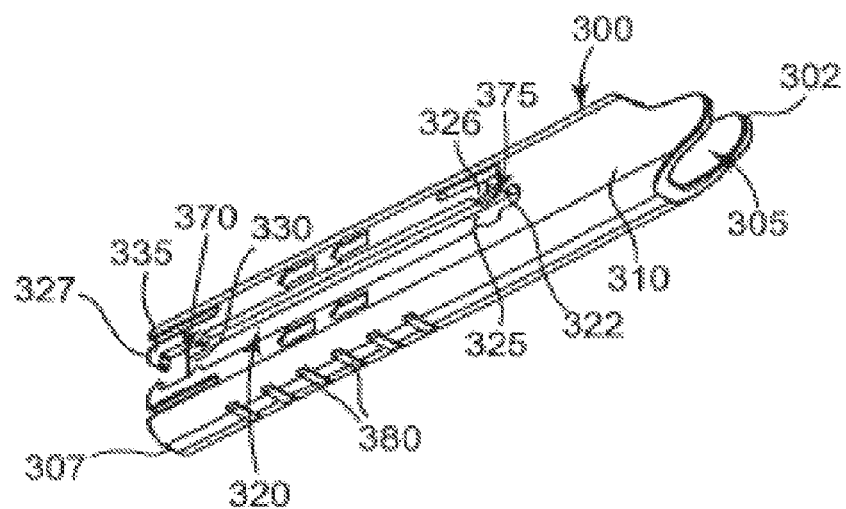
FIG. 3A illustrates a perspective view of a front face of a blade guard in accordance with a preferred embodiment of the present invention.
Figure 3B:
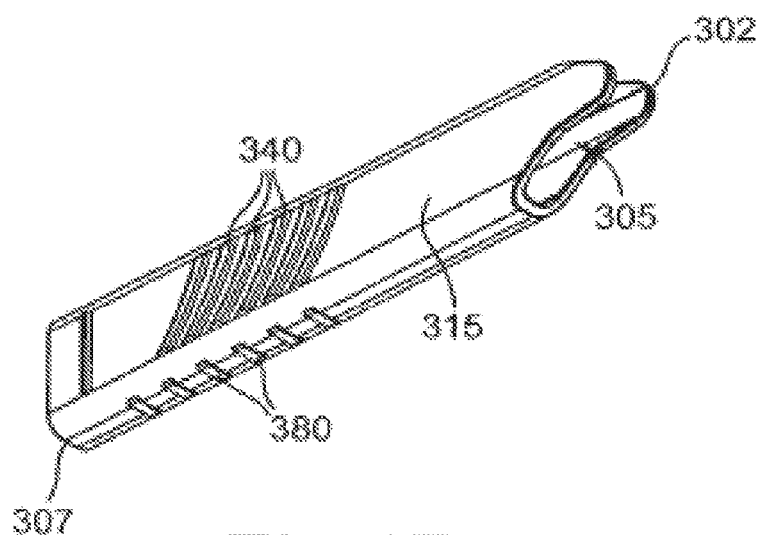
FIG. 3B illustrates a perspective view of a back face of the blade guard of FIG. 3A.
Figure 3C:
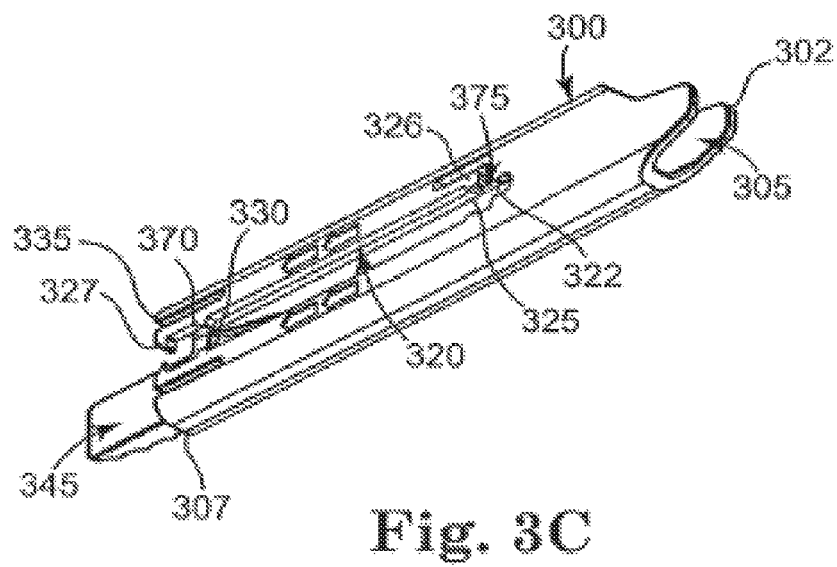
FIG. 3C illustrates a perspective view of a front face of a blade guard in accordance with another preferred embodiment of the present invention.
Figure 3D:
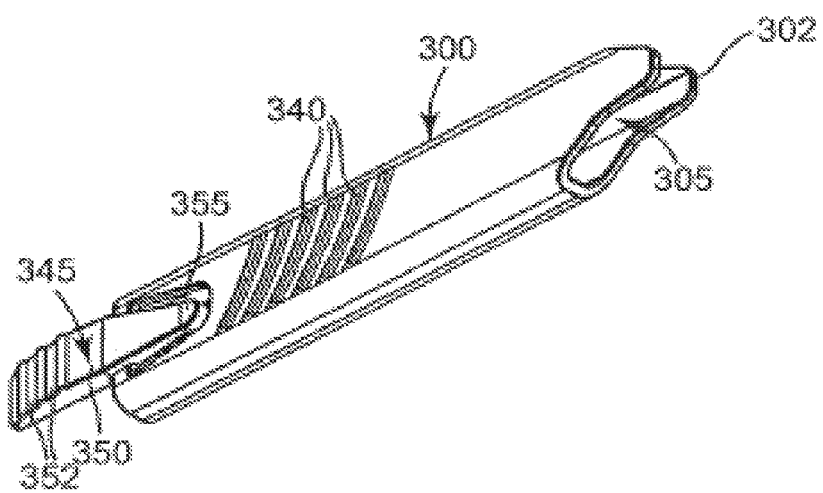
FIG. 3D illustrates a perspective view of a back face of the blade guard of FIG. 3C.

There are at least two preferred embodiments of the blade guard 300. A first embodiment is illustrated in FIGS. 3A-3B, while a second embodiment is illustrated in FIGS. 3C-3E. The embodiment selected can depend on the type of scalpel handle 500 used.

The blade guard 300 comprises an aperture 320 (also referred to herein as slot 320) for providing a track for the holder knob 220 of the blade holder 200 to slide between the closed and open positions. Consequently, as the holder knob 220 moves between retracted and forward positions, the blade 100 moves between the closed and open positions, respectively. More particularly, a directional force applied to the holder knob 220 of the blade holder 200 permits the holder knob 220 to slide along the slot 320 when moving the blade 100 and blade holder 200 between the closed and open positions.

The blade guard 300 defines therein a cavity 305. The blade 100 and blade holder 200 are positioned within the cavity 305 for sliding, when the holder knob 220 slides within the slot 320. The holder knob 220 is positioned near a proximal end 327 of the slot 320 when the blade 100 is in the closed position and the holder knob 220 is positioned near a distal end 322 of the slot 320 when the blade 100 is in the open position.

The blade guard 300 comprises a forward catch 325 and rear catch 330, such that the forward catch 325 is positioned near the distal end 322 of the slot 320 and the rear catch 330 is positioned near the proximal end 327 of the slot 320. The forward catch 325 is adapted to engage the holder knob 220 when the blade 100 is in the open position. The forward catch 325 prevents the blade holder 200 from moving the blade 100 forwardly beyond the open position. The forward catch 325 can include a flexible locking member 326 that locks the blade holder 200, so as to prevent unmistaken unlocking of the blade 100 in the open position. Similarly, the rear catch 330 is adapted to engage the holder knob 220 when the blade 100 is in the closed position. The rear catch 330 can prevent the blade holder 200 from moving the blade 100 rearwardly beyond the closed position. Alternatively, the rear catch 330 prevents the blade holder 200 from moving the blade 100 rearwardly beyond the fully locked position. Further, the rear catch 330 can prevent accidental unlocking of the blade holder 200, in an attempt to prevent accidents.

The blade guard 300 can include a plurality of grooves 340 positioned on the rear face 315 of the blade guard 300, as illustrated in FIGS. 3B and 3D. The plurality of grooves 340 can prevent slippage of the safety scalpel 10 during use.

The blade guard has a front face 310, as shown in FIGS. 3A and 3C, and a back/rear face 315 as shown in FIGS. 3B, 3D, and 3E. The front faces 310 of the two embodiments are preferably the same. The rear face 315, however, can have different attributes.

A beneficial feature of the differing rear faces 315 includes a method of releasing the blade guard 300, and consequently the blade cartridge 400 from the scalpel handle 500.

The blade guard 300 of FIGS. 3C and 3D further includes a latching assembly 345 for releasing the blade guard 300 from the scalpel handle 500. The latching assembly 345 includes a knob 350 extending from the rear face 315 of the blade guard 300, and a locking mechanism 355. The surface of knob 350 can include ridges 352 for increased traction when in contact with a finger during removal of the blade guard from the scalpel handle 500. As described more fully below, the knob 350 is adapted to remove the blade cartridge 400 from the scalpel handle 500.

One skilled in the art will recognize that the blade holder 200 and blade guard 300 can be made of a variety of materials including, but not limited to, plastic, such as acrylonitrile-butadiene-styrene (ABS) copolymer plastic.

As described above, the blade 100 and blade holder 200 fit into the blade guard 300. Collectively, these three elements form the blade cartridge 400. The blade cartridge 400 is attachable to and detachable from a distal end of the scalpel handle 500.

The scalpel handle 500, as shown in FIGS. 1A and 1B, comprises a handle portion 540 and a blade receiving portion 550. The handle portion 540 extends from an approximate midpoint 555 of the scalpel handle 500 to the proximal end 507 of the scalpel handle 500, while the blade receiving portion 550 extends from the approximate midpoint 555 to the distal end 502 of the scalpel handle 500.

The distal end 502 of the scalpel handle 500 can be cut on the front face 510 to accommodate the blade cartridge 400. Preferably, the distal end 502 of the scalpel handle 500 can have a tapered portion 504 for improved assembly of the safety scalpel 10.

The scalpel handle 500 comprises at least one extending member 530 on the front face 510 of the proximal end 557 of the blade receiving portion 550, such as near the approximate midpoint 555. The extending member 530 extends outwardly from the scalpel handle 500 and is adapted to enable the securing of the blade cartridge 400 to the scalpel handle 500.

That is, the at least one extending member, or medial notch, 530 is adapted to engage at least one catch 335 of the blade cartridge 400 (e.g., catch 335 of the blade guard 300). When the blade cartridge 400 is attached to the scalpel handle 500, the catch 335 of the blade cartridge 400 can engage, or snap about, the extending member 530 to prevent longitudinal movement of the blade cartridge 400. In addition, lateral movement of the blade cartridge 400 is limited due to the form fitting blade receiving portion 550.

For increased traction of the scalpel handle 500 when in contact with a finger during use of the safety scalpel 10, the handle portion 550 can include a plurality of grooves 525 positioned on a back face 515 of the scalpel handle 500, as illustrated in FIG. 6C. The plurality of grooves 525 can prevent slippage of the safety scalpel 10 during use.

As illustrated in FIGS. 1A, 1B, 6A, and 6B, the handle portion 550 of the scalpel handle 500 can include indicia 520. The indicia 520 is generally located on the front face 510 and near the proximal end 507 of the scalpel handle 500. While one skilled in the art will recognize that the indicia 520 of the present invention can include multiple markings or printings, the indicia 520 are preferably units of measurement such as, but not limited to, the metric system, the Imperial system, or many other appropriate measuring systems.

The scalpel handle 500 is designed to accept the blade cartridge 400, and provide the user with the feel of a conventional scalpel when used. It is thus provided of materials, weight, and design for comfortable use by the user.

Assembly of Blade Cartridge 400

The blade cartridge 400 includes the fitted cooperation of the blade 100, the blade holder 200 and the blade guard 300, as shown in FIG. 4. Preferably, the blade cartridge 400 is assembled offsite from where the present safety scalpel 10 is ultimately used, for example, in a factory, such that only the assembled blade cartridge 400 is delivered to the user. Also, the blade 100 can be attached to the blade holder 200 through insert molding, wherein the blade holder 200 is actually formed and molded around the blade 100. With the use of insert molding, the blade 100 need not be subsequently attached to the blade holder 200.

The blade cartridge 400 can be delivered in its own sterilized wrapping such as, for example, a foil wrap. Thus, the blade cartridge 400 is not intended for the user to assemble, but is intended only for the mating of the blade cartridge 400 with the scalpel handle 500.

As described above, the blade 100 is fixed to the blade holder 200 by aligning the blade aperture 120 with the corresponding holder protrusion 205 of the blade holder 200. The protrusion notch 215 permits the blade 100 to be secured onto the blade holder 200, as shown in FIGS. 2A and 2B.

The blade holder 200 with the blade 100 is then attached to the blade guard 300 by sliding and slotting the blade holder 200 into the aperture 305 of the blade guard 300. This is shown by the arrow in FIG. 4.

To attach the blade 100 and blade holder 200 into the blade guard 300, the blade 100 and blade holder 200 are inserted into the blade guard 300, such that the blade 100 is aligned within the cavity 305 defined by the lateral sides of the blade guard 300 and the holder knob 220 fits into slot 320. As illustrated in FIG. 4 (see arrow), the blade holder 200 is slotted into the blade guard 300 such that the stopper rib 230 on the blade holder 200 engages the rear retaining slot 370 of the blade guard 300.

The blade holder 200 and the blade 100 are kept temporarily locked in the blade guard 300 by the holder stopper rib 230 engaging and locking to the matching rear retaining slot 370 on the blade guard 300. Accordingly, the blade 100 can be kept in the closed position.

In the assembled blade cartridge 400, the blade 100 is wholly enclosed in the blade guard 300 until mounted on the scalpel handle 500 for use.

Mounting of Blade Cartridge 400 to Scalpel Handle 500

As shown in FIGS. 1A and 1B, the process of mounting the assembled blade cartridge 400 to the scalpel handle 500 is fairly simple. The distal end 502 of the scalpel handle 500, i.e., the blade receiving portion 550, can be inserted into the cavity 305 of the blade cartridge 400, preferably at the proximal end 307. Indeed, the blade receiving portion 550 of the scalpel handle 500 can be housed in the track 240 of the rear face 225 of the blade holder 200 to secure the blade cartridge 400 to the scalpel handle 500. The blade cartridge 400 slides to the point where the catch 335 engages an extending member 530.

Figure 5:
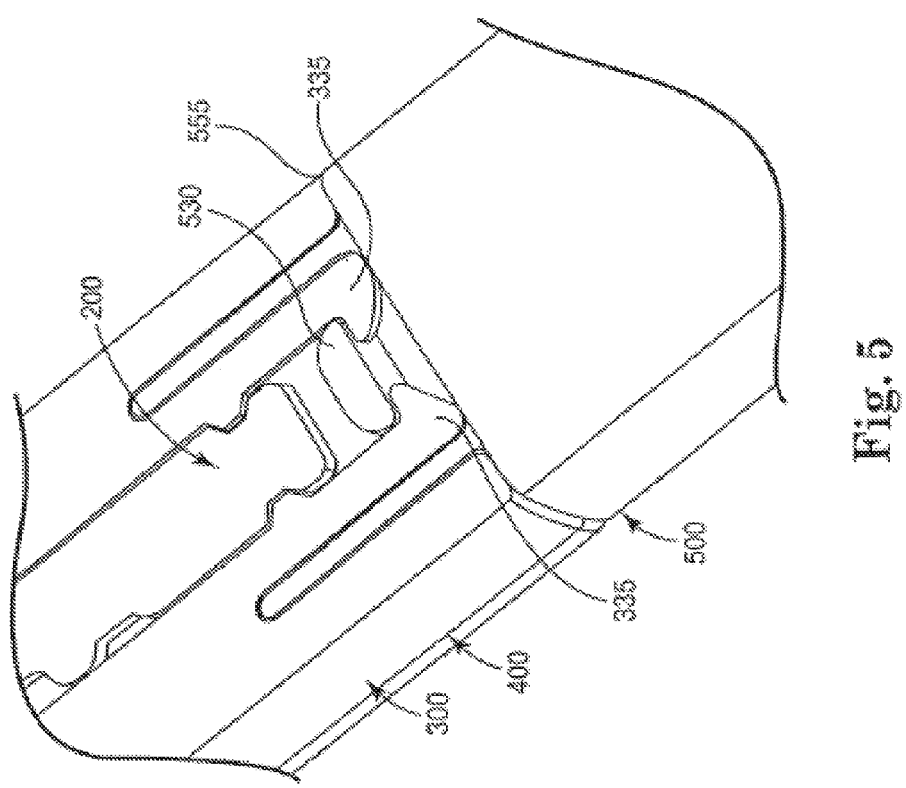
FIG. 5 illustrates a front face, perspective view of the blade cartridge attached to a scalpel handle.

The catch 335 of the blade cartridge 400 is arranged to latch around the extending member 530. Further, the proximal end 307 of the blade cartridge 400 (e.g., proximal end 307 of the blade guard 300) is adapted to abut against the approximate midpoint 555 of the scalpel handle 500, such that the blade cartridge 400 has limited, or no, longitudinal and/or lateral movement. FIG. 5 illustrates a close up of the blade cartridge 400 secured to the scalpel handle 500, such that the catch 335 is latched to the extending member 530.

In addition, when the scalpel handle 500 includes an aperture 505, the blade cartridge 400 can be further secured to the scalpel handle 500. The blade cartridge 400 (e.g., the blade guard 300) can include the latching assembly 345. The latching assembly 345 includes a locking mechanism 355 that engages the aperture 505 of the rear face the scalpel handle 500. This engagement further secures the blade cartridge 400 to the scalpel handle 500.

Use of Safety Scalpel 10

When first mounted, the blade 100 in the blade cartridge 400 is in the closed position, as illustrated in FIGS. 6A and 6C. The blade 100 can be extended out of the blade guard 300 by depressing the holder knob 220 of the blade holder 200 (e.g., pushing the holder knob 220 downward) or alternatively simply pushing outward towards the distal end 202 of the blade holder 200; releasing the stopper rib 230 on the blade holder 200 from the rear retaining slot 370 on the blade guard 300; sliding the holder knob 220 along the slot 320 of the blade guard 300 until the blade 100 reaches the open position, upon which the holder knob 220 is released such that the stopper rib 230 on the blade holder 200 engages the front retaining slot 375 on the blade guard 300. Thus, the blade 100 is temporarily locked in the open position. When the blade guard 300 engages the front retaining slot 375, the flexible locking member 326 can be moved outwardly toward an edge of the blade guard 300, such that it locked.

In this open position, as shown in FIG. 6B, the safety scalpel 10 is ready for use, i.e., cutting and/or slicing. Further, in this position, the blade 100 is prevented from moving laterally and transversally during use of the safety scalpel 10.

The blade cartridge 400 (e.g., the blade guard 300) can further comprise a plurality of indentations 380, as illustrated in FIGS. 1A, 3A, and 3B. The plurality of indentations 380 are positioned on at least one lateral side/edge of the blade guard 300, such that the plurality of indentations 380 provide increased grip of the safety scalpel 10 during use.

If the user needs to hand the safety scalpel 10 to a colleague, she first moves the blade 100 into the closed position by depressing the holder knob 220 on the blade holder 200 to release the stopper rib 230 from the front retaining slot 375. Alternatively, she can move the holder knob 220 towards the proximal end 307 of the blade guard 300. In either case, this causes a sliding of the holder knob 220 back along the slot 320 of the blade guard 300, until the blade 100 reaches the closed position, upon which the holder knob 220 is released such that the stopper rib 230 on the blade holder 200 re-engages the rear retaining slot 370 on the blade guard 300. The blade 100 is now temporarily locked in the closed position. The blade 100 can be moved any number of times between the open and closed positions until the operation is completed.

Dismounting of Blade Cartridge 400 from Scalpel Handle 500

Because there are at least two embodiments of the scalpel handle 500 that can use two different blade guards 300, there are two different processes of dismounting the blade cartridge 400 (e.g., blade guard 300) from the safety handle 500.

In a first embodiment, the blade guard 300 of FIGS. 3A and 3B is secured to the scalpel handle 500 of FIG. 1A. That is, there is no aperture 505 (see FIG. 1B).

The blade guard 300 in this first embodiment is removed by having the holder knob 220 placed in the rear retaining slot 370, such that the blade 100 is in the closed position and does not extend from the blade guard 300. The holder knob 220 can be slid slightly further towards the proximal end 307 of the blade cartridge 400 (e.g., proximal end 307 of the blade guard 300), or towards the approximate midpoint 555. When the holder knob 220 slides in this direction, the catch 335 moves away from the extending member 530 of the scalpel handle 500. This can release the blade cartridge 400 from the scalpel handle 500. Then, the user need only slide the entire blade cartridge 400 towards the distal end 502 of the scalpel handle 500, or off the scalpel handle 500.

In a second embodiment, the scalpel handle 500 includes an aperture 505 in proximity to the extending member 530, preferably slightly offset towards the distal end 502. In this embodiment, the blade cartridge 400 (e.g., the blade guard 300) further includes the locking mechanism 355 about its rear face 315.

Once the locking mechanism 355 is removed from the aperture 505, the catch 335 can be released from the extending member 530, as described above. Then, the blade cartridge 400 is loose enough to be released from the scalpel handle 500. In essence, the latching assembly 345 is an additional safety feature to help ensure the blade cartridge 400 does not mistakenly release from the scalpel handle.

The rear face 315 of the blade cartridge 400 (e.g., the rear face 315 of the blade guard 300) matches up with the rear face 515 of the scalpel handle 500. When the blade cartridge 400 is secured to the scalpel handle 500, the latching assembly 345 is adapted to engage the aperture 505 of the scalpel handle 500. The latching assembly 345 includes the knob 350 and the locking mechanism 355. Because the locking mechanism is an inwardly extending mechanism, it engages the aperture 505 in its normal state. If the knob 350 is depressed, however, the locking mechanism 355 disengages from the aperture 505. The knob 350 can include a plurality of ridges for increased traction in disengaging the locking mechanism 355 from the aperture 505.

Disposable Safety Scalpel 10

In another alternative embodiment of the present invention, the safety scalpel 10 comprises a disposable scalpel handle 500, such that the disposable scalpel handle 500 is separate and passive from the blade cartridge 400. The disposable scalpel handle 500 is adapted to attach to the blade cartridge 400. Preferably, the blade cartridge 400 and the disposable scalpel handle 500 are permanently fixed to each other at the factory during the manufacturing process of the safety scalpel 10. After use, the blade cartridge 400 and disposable scalpel handle 500 can be properly discarded.

Alternative Preferred Embodiment

Figure 8:
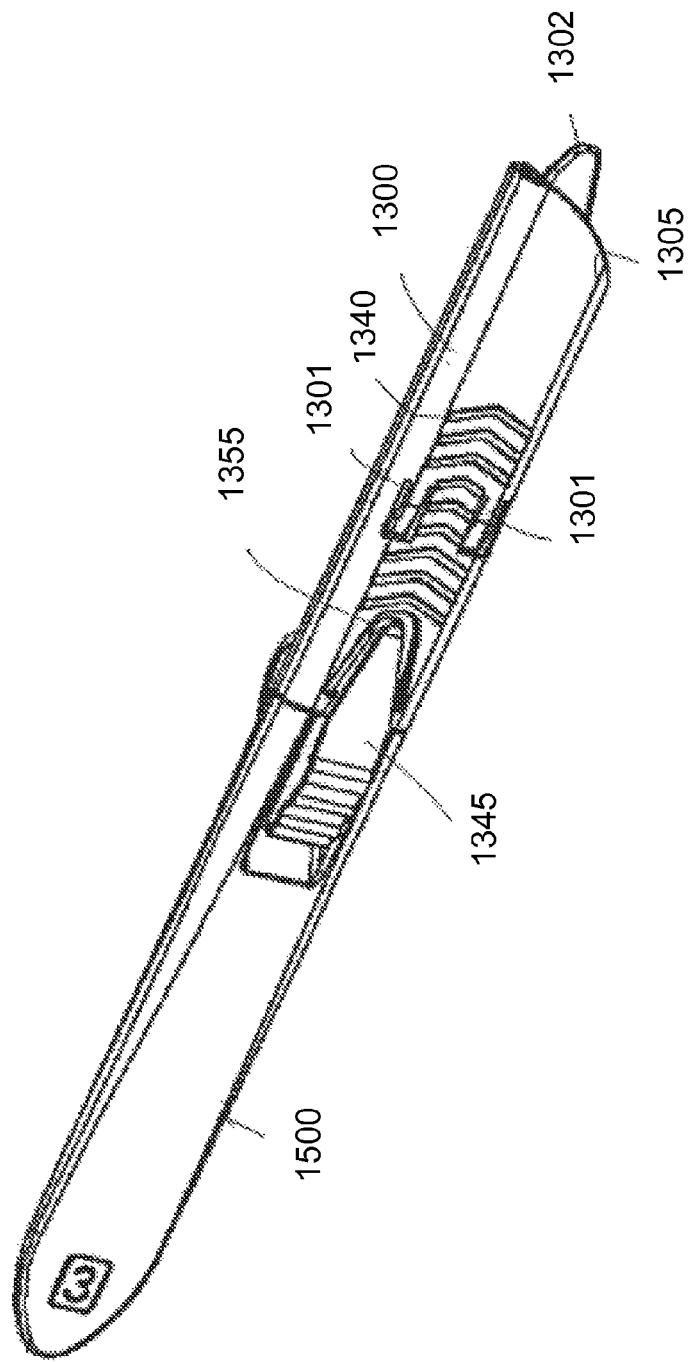
FIG. 8 illustrates a perspective view of the back face of a safety scalpel like that in FIG. 5c except with the blade housed in the blade guard, the blade guard having integrated mechanical stops, in accordance with a preferred embodiment of the present invention.
Figure 9:
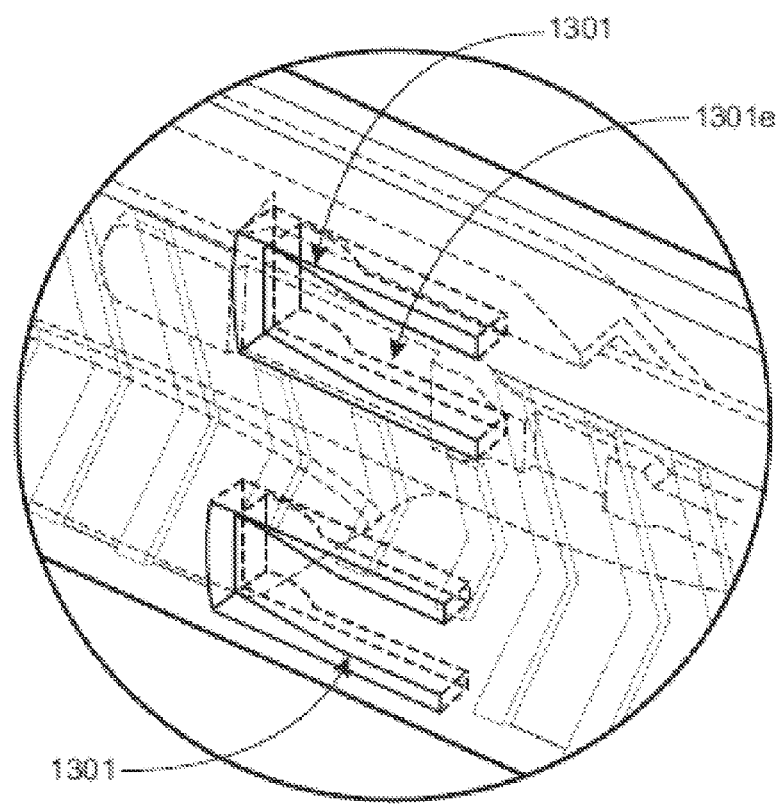
FIG. 9 is a close up fragmentary perspective view of a portion of the view in FIG. 8 magnified to show detail concerning stops 1301.
Figure 10:
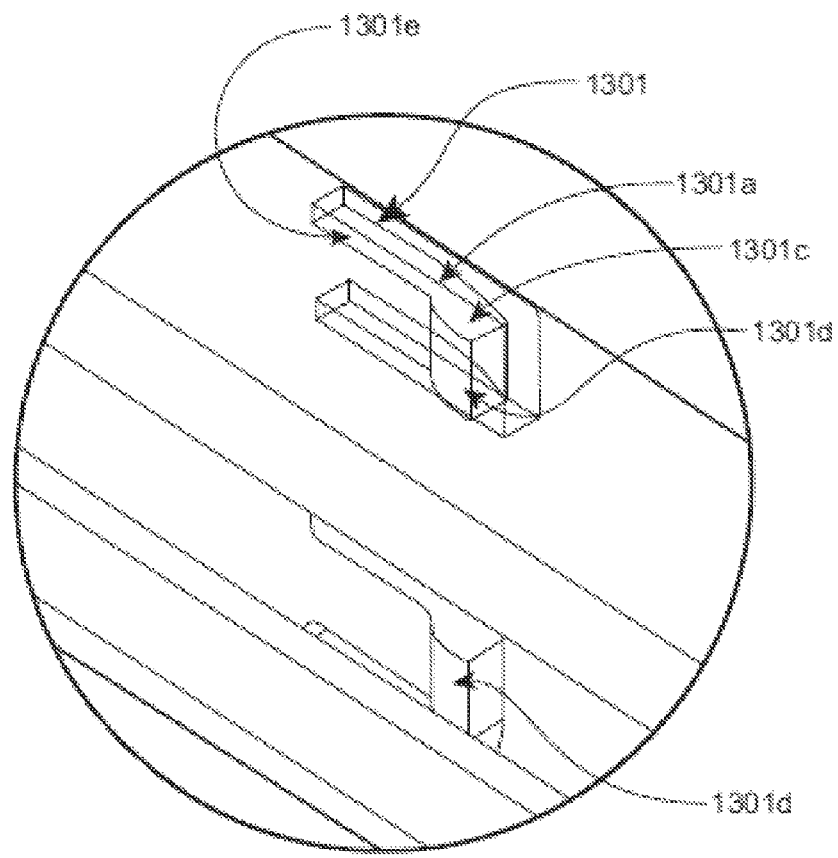
FIG. 10 is a fragmentary close up view like FIG. 9 except from the opposite side.

In order to further increase the safety of the scalpel, the preferred embodiment in FIGS. 8-10 disclose additional features to secure the blade from accidental movement even if the user attempt to operate the device improperly. In describing this embodiment, to the extent it coincides with the prior embodiment, the same reference numerals are used and reference should first be had to the previously described figures. In this embodiment of the present invention the safety scalpel 10 comprises a non-disposable scalpel handle 500, such that the non-disposable scalpel handle 500 is separate and passive from the disposable blade cartridge 400. The non-disposable scalpel handle 500 is adapted to attach to the disposable blade cartridge 400. In this embodiment, for safety reasons, it is preferable to ensure that the scalpel blade 100 remains securely housed within the blade guard 300 when latching assembly 345 is disengaged from catch 355 and the entire blade guard 300 is discarded.

FIG. 8 illustrates a perspective view of the back face of the safety scalpel 10 in accordance with the preferred embodiment of the present invention with the blade 100 (not shown) housed entirely within the blade guard 1300. Components in FIG. 8 that correspond directly with components in FIG. 1A have a prefix "1" added thereto (i.e. increased by 1000). The blade guard 1300 may be made of a plastic-like material and a region of the blade guard 1300 may be configured to protrude into the interior region of the blade guard 1300. The protrusions into the interior region of the blade guard 1300 will hereafter be referred to as mechanical stops or brakes 1301. FIG. 8 shows mechanical stops 1301 located near the edge of the back surface of the blade guard 1300. The mechanical stops 1301 may protrude inboard into space allotted for the scalpel to traverse The stops/guards mechanically secure the scalpel blade 100 directly, or by engagement with the blade holder 200, within the blade guard 300 when the blade guard is removed from the handle 500 This is done by creating frictional contact (i.e. a bias force) between the stops 1301 and holder 200 (or blade 100). In effect stops 1301 are fingers which protrude into the spaced to be occupied by the holder 200, thereby applying a frictional drag thereon. The drag force can preferably be easily overcome by insertion of the handle 500 which lifts the brakes 1301 out of their protrusion into that space. In the preferred construction, the stops 1301 will be "deactivated" when the handle is inserted.

The stops 1301 can be built in many ways and be positioned in may places. The preferred position is shown in FIG. 10. In that embodiment, there are a pair of stops 1301 which are formed in the plastic guard as fingers 1301a which are cut out from the guard material itself and inclined to be biased into the travel path of the scalpel blade.

The fingers are actually two parts. See FIGS. 9-10. A first portion 1301e extending from the plastic housing and being resiliently connected therewith and a second portion 1301c at the distal end, a land, extending into the space of sliding blade. The land is preferably chamfered 1301d (edges rounded/beveled) to prevent the blade from getting stuck (hanging up) when engaging the blade holder 200 and also increases the force per unit area at the contact point.

There are other ways to accomplish this important braking action. First, only one stop may be used. It may also be provided on the sidewall instead of the bottom or top wall as shown. The braking action itself may be accomplished by a friction pad affixed inside of the safety housing or by a magnet embedded in the housing to cause a magnet drag against the steel blade (unless non magnet stainless is used). The scope of this invention includes other mechanical means for stopping the inadvertent movement of the blade once the lock has been released.

The degree of bias and resilience of the fingers should be such that the blade cannot move without being urged by the user, but that insertion of the handle 500 is not obstructed by resistance created by the stops 1301. In practice, the handle can easily lift the stops out of the way when inserted, partly because of the chamfered edges on fingers 1301d.

In one embodiment of the present invention the mechanism by which the mechanical stops 1301 secure the scalpel blade 100 within the blade guard 1300 during disposal thereof is described below.

In preparation of disposing the blade guard 1300, the surgeon may first retract the scalpel blade 100 entirely within the blade guard 1300. Next, the surgeon may begin to disengage the non-disposable scalpel handle 1500 from within the blade guard 1300 by applying force to latching assembly 1345 in a direction towards the distal end 1302 of the blade guard 1300. When the distal end 502 (see FIG. 1, item 502) of the non-disposable scalpel handle 1500 passes underneath the mechanical stops 1301, the mechanical stops may now mechanically engage the stops 1301 and possibly distal end of ridges 223a and 223b (see FIGS. 2C, 2D) of the blade holder 200 and secure the scalpel blade 100 within the blade guard assembly 1300. In the normal surgical use of the safety scalpel 10, when the non-disposable scalpel handle 1500 is inserted into the blade guard 1300 (with enclosed scalpel blade 100) the distal end 502 (see FIG. 1A) of the handle slides along the top surface of ridges 223a and 223b (FIGS. 2C and 2D) of the blade holder 200 until the distal end 502 of the handle first engages the mechanical stops 1301. In one embodiment of the present invention, the mechanical stops may be deformable, and the top surface of the scalpel surface may apply a sufficient force to deform the mechanical stops flush with the surface of the blade guard 1300, thereby interposing the scalpel handle between the mechanical stops 1301 and the ridges of the of the blade holder 200, thereby allowing the scalpel blade to be moved freely within the blade guard 1300 by applying force to holder knob 220 (See FIG. 1A). In a preferred embodiment of the present invention, the mechanical stops 1301 may be located proximate to grooves 1340 in FIG. 8, in this location the mechanical stops 1301 may engage the distal end of ridges 223a and 223b (FIGS. 2C and 2D) in a position where the scalpel blade 100 is abutted near the proximate end 207 (see FIG. 1A) of the blade holder, thereby ensuring the scalpel blade 100 is safely housed entirely within the blade guard 1300.

One skilled in the art will recognize that the disposable scalpel handle 500 can be made of a variety of materials including, but not limited to, plastic, such as acrylonitrile-butadiene-styrene (ABS) copolymer plastic.

In yet another alternative embodiment of the present invention, the safety scalpel 10 comprises a disposable scalpel handle 500 having a slideable blade 100 and blade holder 200 received therein. Accordingly, the blade guard 300 is an integral part of the disposable scalpel handle 500 and, therefore, does not detach from the scalpel handle 500. Further, the entire safety scalpel 10 is disposable after use.

The blade cartridge 400 and scalpel handle 500 can be attached and detached as described above.

One skilled in the art will recognize that the scalpel handle 500 (e.g., the entire safety scalpel 10, minus the blade 100) can be made of a variety of materials including, but not limited to, plastic, such as acrylonitrile-butadiene-styrene (ABS) copolymer plastic.

Figure 11:
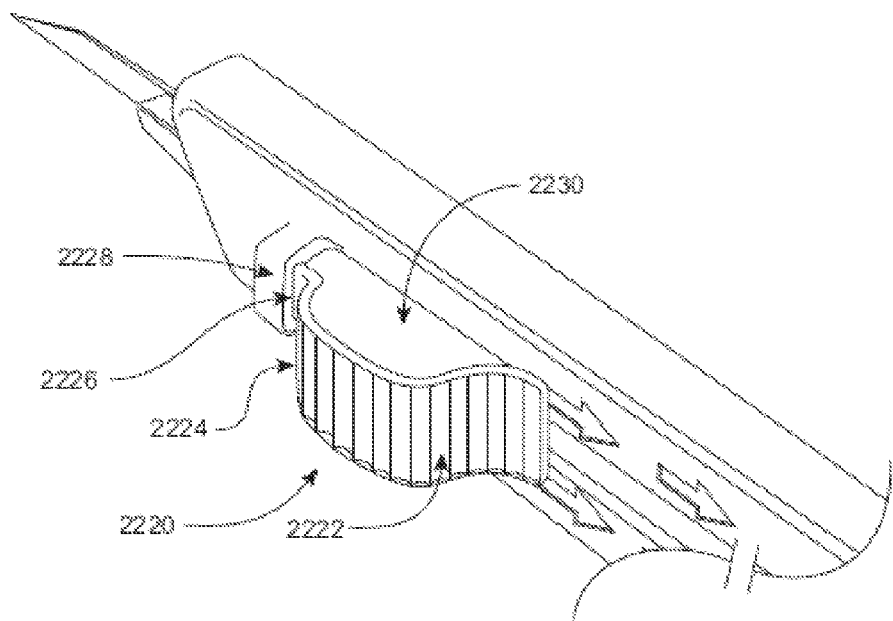
FIG. 11 is a fragmentary close up view of a portion of another embodiment of the safety scalpel.

FIG. 11 illustrates a further safety feature as an alternative to the knob slider 220 in FIG. 1A.

In general terms, there may be a safety catch for preventing accidental retraction of the blade when in use, having a slider knob at least partly external to the blade guard and in mechanical communication with the blade, so that movement of the slider causes movement of the blade, said slider including a base portion and releaseable engagement portion, a catch portion sized to receive said engagement portion, said catch located on said guard such that said catch and engagement portion are engaged when the blade is in a fully extended position.

In addition the safety feature may include a resilient portion extending from said base, having a free end and being spaced apart from said base. The resilient portion may arcuate and depressible and include a catch at its free end and wherein said catch portion includes a receiver sized to receive said catch, so that when said resilient portion is undepressed, said catch may be engaged within said receiver thereby preventing movement of the blade.

In place of slider knob 220 is a compressible slider 2220 which provides a means for the user to extend or retract the blade. FIG. 11 shows the blade in a fully extended position. In addition to other means provided for herein, slider 2220 provides an additional locking means for preventing the blade from retracting accidentally. Slider 2220 may include ridges 2222 to provide good frictional grip. Extending from the base of the slide is a resilient loop 2224 which is preferably attached at one end of the base of the slider and free at the other. The free end includes a hook like structure 2226 which is in the form of a one way barb or a mere land extending radially away from the free end loop 2224, for example, a land extending orthonally from the base of the free end to form a right angle of flat surfaces. On the distal side of the land, the surface may be chamfered or rounded to allow the land to slide under the bridge with less resistance.

Loop 2224 is preferably formed in an arcuate shape or at least spaced from the base 2230 of the slider. This provides a gap for the resilient loop to flex within. By applying pressure to the loop, the hook/barb is depressed an it will easily slide under the gate 2228 which is a receiving channel or bridge sized to receive the hook/barb. When pressure is released from the loop, it returns to its stead state position where the barb 2226 is engaged with a sidewall of the bridge 2228 such that retraction of the blade is prevented unless the user further depresses loop 2224 to release the hook 2226 from the gate 2228 long enough to withdraw the hook backwards out of the gate.

In this manner a further safety feature may be included in the scalpel which prevents unexpected retraction of the blade when in use but provides easy of retraction when desired.

While the invention has been disclosed in its preferred forms, it will be apparent to those skilled in the art that many modifications, additions, and deletions can be made therein without departing from the spirit and scope of the invention and its equivalents, as set forth in the following claims.

We claim:

1. A safety scalpel comprising:
   a disposable blade cartridge comprising:
      a blade;
      a blade holder in communication with the blade; and
      a blade guard adapted to receive the blade and blade holder; and
   a reusable scalpel handle having a distal end,
   wherein the blade holder comprises a track in a rear face of the blade holder opposite a surface of the blade holder for holding the blade, the track including the rear face and a plurality of ridges arranged to slidably receive and house a blade receiving portion of the scalpel handle, the track extending through the blade holder such that the track has openings on both ends, and wherein during movement of the blade relative to the blade guard the ridges of the track of the blade holder slide along the blade receiving portion of the scalpel handle such that the blade receiving portion slides between the ridges of the track and extends through both of the openings of the track; and
   wherein the disposable blade cartridge is lockable to the reusable scalpel handle, and wherein the blade guard includes a mechanical brake arranged to apply a frictional force on the track of the blade holder to prevent movement of the blade relative to the blade guard, the mechanical brake further configured to deform upon engagement with the distal end of the scalpel handle to remove the frictional force from the track to allow movement of the blade relative to the blade guard.

2. The safety scalpel of claim 1, wherein the scalpel handle includes an extending member, wherein the disposable blade cartridge includes a catch for engaging the extending member, and wherein the catch engaging the extending member locks the disposable blade cartridge to the scalpel handle.

3. The safety scalpel of claim 1, wherein the blade holder further comprises a holder knob, the blade moveable from a closed position, wherein the blade is not exposed beyond the disposable blade cartridge, to an open position, and wherein the blade is exposed beyond the disposable blade cartridge.

4. The safety scalpel of claim 1, wherein the scalpel handle includes an extending member, wherein the disposable blade cartridge includes a catch for engaging the extending member,
   wherein the catch engaging the extending member locks the disposable blade cartridge to the scalpel handle, and
   wherein the blade holder further comprises a holder knob, the holder knob enabling the blade to move from a closed position, wherein the blade is not exposed beyond the disposable blade cartridge, to an open position, wherein the blade is exposed beyond the disposable blade cartridge.

5. The safety scalpel of claim 1, wherein the disposable blade cartridge further comprises a latching assembly comprising a locking mechanism that is adapted to engage an aperture of the scalpel handle, such that the latching assembly locks the blade cartridge to the scalpel handle.

6. The safety scalpel of claim 1 wherein said mechanical brake includes at least one element which supplies frictional force to prevent movement of the blade only when the handle is removed.

7. The scalpel of claim 6 wherein the cartridge includes a space for receiving said handle and wherein said brake element includes a finger which flexibly protrudes into said space allowed for the handle, whereby the brake is prevented from interfering with the movement of the blade.

8. The scalpel of claim 7 wherein said finger is configured to flexibly engage at least a portion of the blade holder when said handle is not in place, thereby preventing movement of the blade without the handle.

9. The scalpel of claim 7 wherein said finger includes a contact land, said land having a chamfered surface proximate the point where said land contacts said blade holder when so engaged.

10. The scalpel of claim 1 further including a safety catch for preventing accidental retraction of the blade when in use, comprising:
   a. a slider knob at least partly external to the blade guard and in mechanical communication with the blade, so that movement of the slider causes movement of the blade,
   b. said slider including a base portion and releaseable engagement portion
   c. a catch portion sized to receive said engagement portion, said catch located on said guard such that said catch and engagement portion are engaged when the blade is in a fully extended position.

11. The scalpel of claim 10 wherein said engagement portion includes a resilient portion extending from said base, having a free end and being spaced apart from said base.

12. The scalpel of claim 11 wherein said resilient portion is arcuate and depressible and includes a catch at its free end and wherein said catch portion includes a receiver sized to receive said catch, so that when said resilient portion is undepressed, said catch may be engaged within said receiver thereby preventing movement of the blade.

13. A safety scalpel comprising:
a scalpel handle having a longitudinal axis and a distal end;
a blade cartridge attachable to the scalpel handle, the blade cartridge having:
   a blade guard; and
   a blade holder for holding a blade and a track in a rear face of the blade holder opposite a surface of the blade holder for holding the blade, the track including the rear face and a plurality of ridges arranged to slidably receive and house a blade receiving portion of the scalpel handle, the track extending through the blade holder such that the track has openings on both ends, and wherein during movement of the blade relative to the blade guard the ridges of the track of the blade holder slide along the blade receiving portion of the scalpel handle such that the blade receiving portion slides between the ridges of the track and extends through both of the openings of the track; and
wherein the blade guard includes a mechanical brake arranged to apply a frictional force on the track of the blade holder to prevent movement of the blade relative to the blade guard, the mechanical brake further is configured to deform upon engagement with the distal end of the scalpel handle to remove the frictional force from the track to allow movement of the blade relative to the blade guard.

* * * * *